United States Patent
Caprio et al.

(10) Patent No.: US 9,428,426 B2
(45) Date of Patent: Aug. 30, 2016

(54) PLANT AND METHOD FOR ORGANIC WASTE BIOCONVERSION AND MUNICIPAL WASTE BIOSTABILIZATION

(75) Inventors: Francesco Caprio, Valenzano (IT); Daniele De Gennaro, Molfetta (IT); Giovanni Gorgone, Matera (IT); Massimiliano Roncone, Bitritto (IT)

(73) Assignee: Bioconversion, S.r.l., Valenzano (BA) (IT)

( * ) Notice: Subject to any disclaimer, the term of this patent is extended or adjusted under 35 U.S.C. 154(b) by 108 days.

(21) Appl. No.: 13/820,518

(22) PCT Filed: Aug. 31, 2011

(86) PCT No.: PCT/IB2011/053823
§ 371 (c)(1),
(2), (4) Date: Mar. 29, 2013

(87) PCT Pub. No.: WO2012/029041
PCT Pub. Date: Mar. 8, 2012

(65) Prior Publication Data
US 2013/0206071 A1   Aug. 15, 2013

(30) Foreign Application Priority Data

Sep. 3, 2010   (IT) .............................. BA2010A0032

(51) Int. Cl.
| | |
|---|---|
| C05F 17/00 | (2006.01) |
| C05F 9/04 | (2006.01) |
| A01K 67/033 | (2006.01) |
| C05C 11/00 | (2006.01) |

(52) U.S. Cl.
CPC ......... *C05F 17/0009* (2013.01); *A01K 67/033* (2013.01); *C05C 11/00* (2013.01); *Y02P 20/129* (2015.11); *Y02P 20/145* (2015.11); *Y02W 30/43* (2015.05)

(58) Field of Classification Search
CPC .... C12M 21/04; C12M 41/18; C12M 41/24; C02F 3/00; C02F 11/00
See application file for complete search history.

(56) References Cited

U.S. PATENT DOCUMENTS

| | | | |
|---|---|---|---|
| 5,759,224 A | 6/1998 | Olivier | |
| 6,001,146 A | 12/1999 | Olivier | |
| 6,391,620 B1 * | 5/2002 | Olivier | ....................... 435/262.5 |
| 6,579,713 B2 | 6/2003 | Olivier | |
| 6,780,637 B2 | 8/2004 | Olivier | |
| 2002/0079266 A1 * | 6/2002 | Ainsworth et al. | ........... 210/603 |
| 2002/0144658 A1 * | 10/2002 | Holcombe et al. | ............ 119/6.7 |
| 2004/0029262 A1 * | 2/2004 | Walker | ....................... 435/290.1 |

* cited by examiner

*Primary Examiner* — Nathan Bowers
(74) *Attorney, Agent, or Firm* — R. Ruschena Patent Agent, LLC

(57) ABSTRACT

System for the bio-treatment of organic waste by means of insect larvae comprising a tank provided with removable cover and means for ventilation and temperature control able to induce migration of the larvae outside the waste mass when in a desired larval development stadium, means for distributing in many times the various waste layers and for removing the same at the end of the treatment and means for distributing the larvae inside the tank and for collecting and storing the larvae at the end of the treatment. Method for the bio-treatment of organic waste by means of larval stadium insects provided with the step of placing a first waste layer inside a tank (1), placing insect larvae or eggs on said layer and adding other waste layers at prefixed and shorter time intervals than the larvae development time, inducing the spontaneous migration of the larvae towards suitable collecting areas by means of temperature and humidity control and removing the treated waste from the tank.

15 Claims, 2 Drawing Sheets

PLANT AND METHOD FOR ORGANIC WASTE BIOCONVERSION AND MUNICIPAL WASTE BIOSTABILIZATION

The present invention relates to a system and a method for the bio-conversion of organic waste and for the bio-stabilization of undifferentiated urban solid waste.

At the state of the art, some applications are known wherein larvae of various insect kinds are used for the treatment of urban solid waste. For little quantities of waste, there are also known methods which use earthworms which are left in waste in specific temperature and humidity conditions for long time (even 30 days). It is clear that such methods cannot be applied to great quantities of waste. In U.S. Pat. No. 5,759,224 it is described an apparatus and method for the continuous waste treatment by means of fly larvae. The cited document describes a system made up of a conveyor belt, a means for distributing the waste triturated in grains of dimension equal to maximum twice the mouth of an adult larva on the conveyor belt, a means for placing the fly larvae on the same waste, a means for removing the larvae from the waste at the end of the digestion process and a means for removing the same waste from the conveyor belt. The invention is applied to the treatment of "great quantities of putrescent humid waste". The described method consists in placing the waste in a suitable area of the conveyor belt and in placing the larvae (or their eggs) thereon. While the waste is transported on the conveyor belt, the larvae eat said waste thus converting them in "odourless, more or less dry compost". Since the larvae tend spontaneously to move away from the hot spots, by exploiting this feature of theirs and so by applying heat through infrared lamps in the areas of the compost which are intended to be left, the same larvae are induced to collect at the edges of the conveyor belt, where they fall in the provided collecting channels. The larvae are then transported by means of a water flow by said collecting channels towards some accumulation containers, in which they are separated from the water used for their transportation by means of sieves.

In U.S. Pat. No. 6,001,146, which follows the yet cited document, there is described the same method of treatment, which can be applied to "waste of human food, waste of canning industry and slaughter, human and animal derived slurry", specifying that the waste treatment occurs in a substantially closed chamber with air filtering for removing undesired unpleasant smells.

In the U.S. Pat. No. 6,391,620 it is described a method for the continuous bio-conversion of putrescent waste whose feature is that while a living organism bio-converts the putrescent waste in the superficial portion of the waste heap, the yet bio-converted underlying portion is removed by means of a digging system.

In the U.S. Pat. No. 6,579,713, in addition to what stated in the previous patent it is described a system for removing water by dropping from the waste, and the following draining system. The described system for displacing waste is made up of a blade keyed to a chain moved by a motor.

At the state of the art, there are some applications aiming at the treatment of little waste quantities by means of *Hermetia Illucens* larvae. In the U.S. Pat. No. 6,780,637 it is described a domestic system for waste treatment, which substantially consists of a waste collecting container (slurry or humid waste) provided inside with an inclined surface (ramp like) which is climbed by the *Hermetia Illucens* larvae, which afterwards by means of a suitable duct slip in a container for the collection of the same larvae.

The applications known at the state of the art are limited since they allow only the waste treatment in continuous mode, thus needing room for storing the compost produced continuously by the system and which waits for the transport, which in turn can occur economically only when a certain quantity of treated waste is reached. The only system which provides a batch treatment, i.e. the periodic filling and empting of the container where the waste treatment occurs, i.e. the U.S. Pat. No. 6,780,637, is substantially thought for domestic applications, since, if applied on a large scale, it is disadvantageous for the manual management of a great number of containers with clear limitation on the quantity of treatable waste. Another drawback of said system is that the treatment units are not thermally controlled, therefore the method can be applied only in climatic areas where generally the climatic conditions favour the larval development.

Moreover, the applications known at the state of the art aim at the continuous organic waste treatment, particularly referring to the human and animal derived waste and to the food industry waste, not considering other kinds of waste which are difficult to be disposed of and to which it is possible to apply successfully the method described in the following.

Object of the present invention is to provide an automatic system and a method for the bio-treatment of various nature organic waste by means of insect larvae by means of a bio-reactor able to accumulate therein the compost produced by the waste treatment. Another object of the present invention is the use of species and combinations of species of larval stadium diptera for the application of said bio-treatment method, which are to be selected according to the matrix or combination of organic matrixes to be treated. Moreover said automatic system is designed to adapt its own cycle to the habits and life cycle of the living organisms used. Another object of the present invention is the application of said method for the treatment of specific waste categories for which no satisfying treatment techniques are known at the state of the art. These and other advantages will be clear from the following description which is based on the appended drawings.

Figure 1:
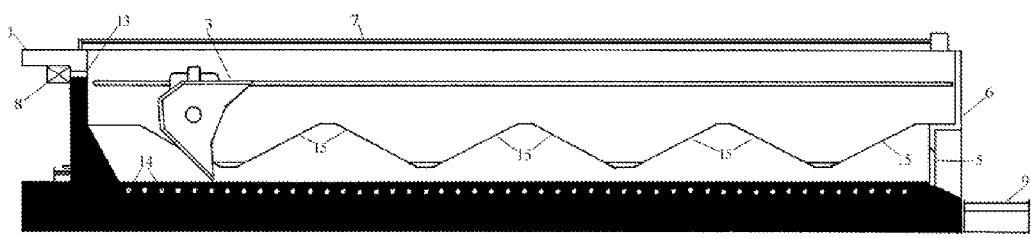
FIG. 1 shows a longitudinal section of the waste treatment tank.
Figure 2:
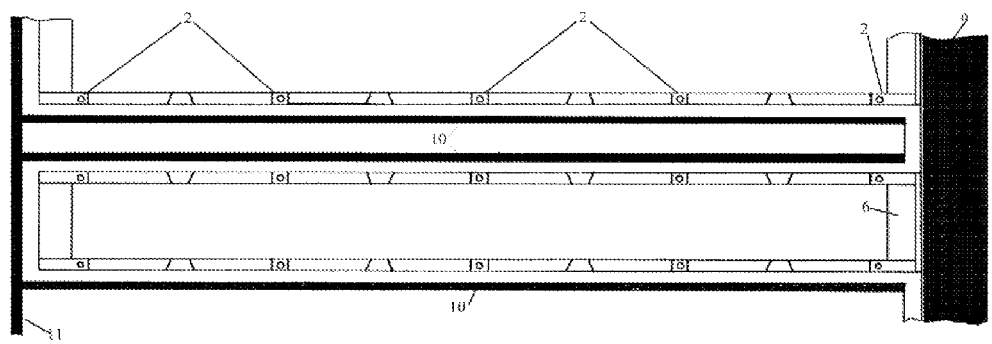
FIG. 2 shows a plan section of the waste treatment tank.

As it is shown in FIG. 1, the system comprises at least a tank (1) for the waste bio-treatment. As a way of example and without limiting the possibilities of usage of tanks shaped differently as the parallelepiped or differently dimensioned as those indicated below, a possible order of magnitude of the described system is between 1-2 meters in width and height and between 5-20 meters in length.

The system functions distributing a layer of waste on the bottom of the tank (1) by means of the bucket (3). In some cases, according to the matrix to be treated, before being introduced in the bio-reactors, said waste can need a pre-treatment step constituted, for example and without applicability limitations, by a grinding and/or homogenization step, a possible following solid/liquid separation and/or a following addition of *Bacillus* bacteria with or without incubation; said incubation meaning for example and without applicability limitations that the waste-bacteria mix remains in the treatment tank in controlled climatic conditions useful for the development of the bacteria strains used.

After the waste is placed with or without pre-treatment on the bottom of the tank, a suitable number of new-born larvae or eggs is distributed in the tank (1). The distribution of the new-born larvae or eggs can occur by means of an automatic distributor, not shown in the drawings, where the larvae are stored in controlled climatic conditions in order to minimize the frequency of supplying said larvae or eggs from the breeding site. The treatment cycle continues by dumping at fixed time intervals, for example daily, a layer of waste by means of the bucket (3), which can slide on the longitudinal guide (4) in a motorized way. Then the daily distribution of waste to be treated continues until the development cycle of the larvae, which spontaneously migrate outside the waste heap before becoming pupas, is over.

The spontaneous migration of the larvae occurs by means of ramps (15) which emerge from the mass treated and on whose top it is located the funnel mouth (2) of the larvae collectors (12). Alternatively, as a way of not limiting example, in the treatment of urban solid waste or of other matrixes if advantageous, the migration of larvae or pre-pupas can occur through the same walls of the bio-reactor, through holes with controlled opening (not shown in figure), with diameter preferably between minimum 1 mm and maximum 50 mm. The larvae or pre-pupas migrating through the holed walls are collected by ramps (not shown in figure), from which they fall directly on the conveyor belt (10).

The migration is accelerated by the fact that in the collecting compartment is provided a different controlled climatic habitat, which will be better described in the following, and that the larvae and pre-pupas tend to migrate naturally towards dry or humid places according to the species attitude which induce them to look for a habitat suitable for becoming pupa; therefore climatic conditions suitable to favour the migration of the same will be used each time according to the species or mix of species used.

The ramps (15) are provided with an inclination variable according to the species whose larvae are used for the treatment. A typical inclination, as a way of example, is 30° for the "auto-collection" of the *Hermetia Illunces* larvae in pre-pupa stadium. The height of the ramp top, the duration of the larvae development cycle and the quantity of waste treatable by the bio-reactor are related to one other.

In fact, the quantity of waste daily admitted in the bio-reactor (1) is such that at the end of the larvae development cycle, the waste heap reaches almost the height of the top of the ramp (15). Said quantity varies day after day according to the larvae development stadium and their consequent need of daily nutrition.

Figure 3:
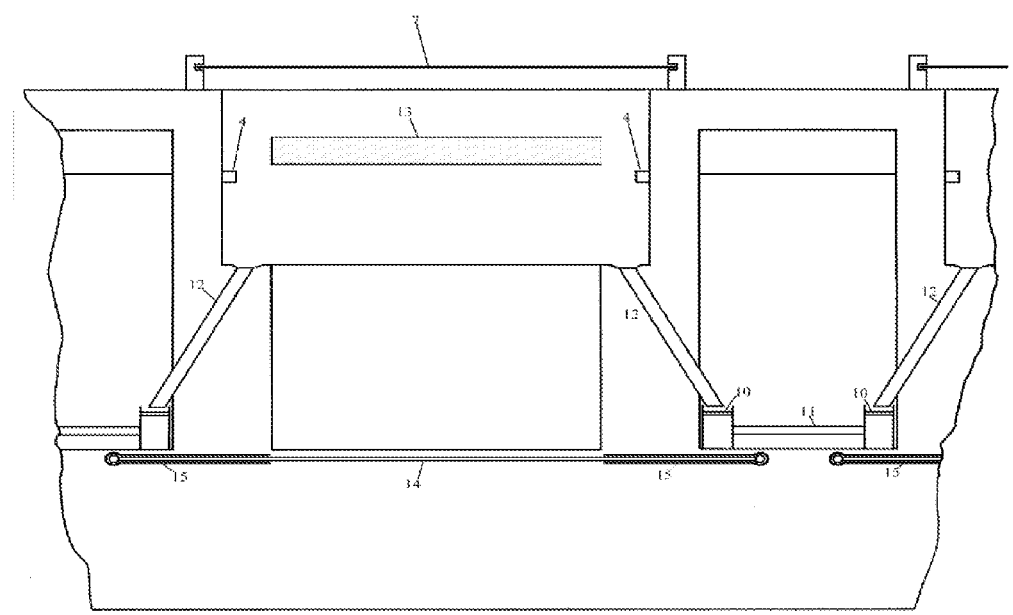
FIG. 3 shows a cross section of the waste treatment tank.

As it is well visible in FIG. 3, by means of the collectors (12), the larvae arrive on a first conveyor belt (10), which then conveys them on a second conveyor belt (11) from which they are conveyed to the post-treatment systems. The larvae and the pre-pupas grown at the end of the waste treatment cycle described, provided by means of the system object of the present invention, can in fact be dried or frozen to be then used as fodder, as additive. Another possible use of the larvae or pre-pupas grown at the end of the waste treatment cycle, as a way of not limiting example of the *Hermetia Illucens* larvae or pre-pupas is the production of acid fats which can occur with any one of the fat extraction techniques known at the state of the art, as for example the use of supercritical fluids. Alternatively, the larvae or pre-pupas can be used for the extraction of the substances which they are composed of, which are useful for example for the production of conditioners for biodiesel and diesel and in the production of polymeric and bio-polymeric films.

As yet stated, the larvae or pupas are able to migrate autonomously towards environments with favorable climatic conditions, however the provision of conveyor belts (10, 11) is useful to optimize the larvae collection process, and to avoid that they lose weight and so value while moving.

As it is shown in FIG. 3, the bio-conversion process occurs inside the bio-reactor (1) covered by a sliding covering cloth (7) with reduced heat transmission coefficient. Said cloth can be substituted by a rigid cover (not shown in figure), which can be packaged and provided with reduced heat transmission coefficient. In many points on said cover, controlled opening traps can be provided for capturing the saprophage diptera (not shown in figure). Said traps can be provided also on the walls of the tanks or close thereto. The provision of said traps contributes simultaneously to kill the population of pest diptera, where the bio-reactors are used, and to increase the larval population used for the bio-conversion treatment. Said traps opening time for possible diptera to be admitted therein, the so-called "engagement time" can vary preferably from one to three days, starting from the first waste layer deposition in the tank. In the vertical walls of the tank it is possible to integrate ventilation openings of suitable dimension. A forced suction system (8) sucks air from the bio-reactor through the air inlet (13) and delivers it to a filtering system, not shown in figure, to control the humidity level in the bio-reactor and to avoid unpleasant smells to be dispersed in the environment. The air admitted through the cited openings is pre-heated if needed by means of heat exchange systems, not shown in figure.

The temperature and humidity climatic conditions of the process are controlled by means of the forced suction system (8) and a temperature control system (14). As a way of example in FIG. 1 and FIG. 3 it is shown a temperature control system (14) provided in the bottom of the tank by means of pipes, which are insulated by means of an insulation (16) at the inter-tank passages to limit the heat dispersion, in which a temperature controlled thermal-vector fluid flows. The climatic conditions provided by the heat and air flows are selected in order to guarantee the maximum efficiency of the treatment process or to make it independent from the outer climatic conditions.

The product of the waste digestion, the so-called "compost", is removed at the end of the treatment by means of the same bucket (3) used for distributing daily the waste in the bio-reactor, which drags the compost in many passages towards the end of the bio-reactor where the partitions (5) and (6) are open and in particular the lower partition (5), by bouncing, acts as side to convey the compost on the transfer roll (9). The roll (9) transfers the compost to the units for post-treatments as for example the squeezing treatment for the extraction of liquid phase directly usable as fertilizer in agriculture or for example a further treatment in a bio-reactor with different climatic conditions for further bio-conversion by means of other saprophage organisms, for example *Eisenia foetida, Lumbricus terrestris* etc. . . .

During the step of compost collecting or waste distribution, the larvae collectors (12) can be covered temporarily by lids which avoid possible penetrations of the compost or waste in the larvae collection and treatment circuit. After the compost collection, the bio-reactor (1) can be washed with water conveyed towards the post-treatment units through the same transfer roll (9).

In a system where many bio-reactors (1) are provided, the passage (15) between the bio-reactors allows the access to the transfer rolls (10) of the larvae in pupa stadium and to the thermal system. In the inter-tank passage it is possible to arrange a first system for larvae post-treatment.

The just described method can be successfully applied to a wide range of waste. It is also possible its application to the creation of engineered food chains for the development and innovation in the zoo-technical field. The engineered food chains are controlled transformation streams of organic matter inside any productive food supply chain, where it is possible to recover the organic material previously considered as waste, in order to admit it again in the same process flow or in another connected thereto, thus closing the "food chain". As a way of example the method object of the present invention can be used in the dairy food supply chain, where the zoo-technical waste can be mixed to the ones derived by the milk transformation to optimize qualitatively and quantitatively the larvae growth during the bio-conversion process, in order to produce a better and greater larvae and pre-pupas biomass, which, supplied on such combination matrixes, can represent a nutraceutical additive in the nutrition of the species provided in the integrated breeding.

The invention claimed is:

1. A system for the bio-treatment of organic waste using insect larvae and eggs, comprising:
    at least a container (1) provided with a ventilation system (8) and a temperature control system (14),
    at least one automatic waste distribution system which operates for distributing the waste to be treated inside said container (1) and for removing the digested waste at the end of the treatment by dragging said digested waste through a plurality of passages toward the end of said container (1) where it is removed by opening partitions (5, 6) and using a transfer roll (9) which also allows the washing of the container (1) by conveying water and provides transferring of said treated waste for a post-treatment to extract agricultural fertilizer;
    an automatic system for distributing said larvae or larvae eggs inside said container (1) containing waste, wherein said distribution occurs using an automatic distributor where said larvae or larvae eggs are stored in controlled climatic conditions to minimize the supplying frequency from a breeding site;
    a system for collecting and storing said larvae (2, 10, 11, 12, 15) after the same are used for the waste treatment, wherein said system for collecting and storing larvae further comprises a subsystem able to induce the migration of the larvae in a desired stadium of development outside the waste mass providing a different controlled climatic habitat, dry or humid, according to the species attitude to generate an habitat suitable for said larvae to become pupas inside the collecting compartment and inside said automatic waste distribution system;
    and wherein said container (1) is configured so that said automatic waste distribution system can introduce waste inside said container (1), dumping the new waste to be treated over the waste layers yet treated by said larvae;
    and wherein said system for the bio-treatment of organic waste is using species and combinations of species of larval stadium diptera to provide for the treatment of specific waste categories;
    and wherein said container (1) is a tank provided on the upper surface with a removable sliding cover (7) and is shaped approximately as a parallelepiped, with between 1 and 2 meters width, and between 5 and 20 meters length;
    and wherein said removable sliding cover (7) is made UP of a sliding covering cloth with reduced heat transmission coefficient and having controlled opening traps for capturing saprophage dipters; and wherein said controlled opening traps have an opening time, for possible diptera admission, varying between one and three days, starting from the first waste layer deposition inside said container (1);
    and wherein said traps are also provided on the walls of the container (1) to contribute to kill the local population of pest diptera and increase the larval population used for bio-conversion treatment.

2. System according to claim 1, further comprising a controlled temperature and humidity storage system for larvae or eggs conservation.

3. System according any one of claim 1, wherein said ventilation system (8) comprises a fan sucking air from said container (1) by way of a suitable air inlet (13) and conveys it to a filtering and smell removing system.

4. System according to claim 1, wherein said container (1) has walls with ventilation openings provided for air admission from outside, wherein the air admitted through said openings is being pre-heated by a system which allows the heat to be recovered by heat exchange with the air ejected by said ventilation system (8).

5. System according to claim 1, wherein said temperature control system (14) inside the container (1) comprises a series of insulated pipes located at the bottom of the container (1) where a temperature controlled thermal-vector fluid flows to provide thermal independency from outer climatic conditions.

6. System according to claim 1, wherein said automatic waste distribution system comprise a bucket (3) for distributing a layer of waste on the bottom of said container (1), said bucket (3) which can slide in a motorized way on longitudinal guides (4) configured so that the bucket (3) is allowed to operate on the whole extension of said container (1); and wherein said same bucket (3) is used for the removal of the treated waste at the end of the waste treatment by dragging said treated waste in many passages towards the end of said container (1) where partitions (5, 6) are opened.

7. System according to claim 1, wherein said system for collecting and storing said larvae (2, 10, 11, 12, 15) after the same are used for the waste treatment, comprises ramps (15) to facilitate the migration of the larvae from the larvae collectors (12) provided with funnel openings (2) and a system of conveyor belts (10, 11); wherein said larvae collectors (12) are temporarily covered by lids to prevent penetration of waste into said larvae collectors (12) and treatment circuit.

8. System according to claim 7, wherein said system which facilitates the migration of the larvae and their collection and storage comprises a plurality of holes with controlled openings provided in the side walls of said container (1) configured so that the larvae are allowed to go out from said container (1) through said holes without dragging waste, inclined tracks for collecting the larvae once gone out, and a conveyor belt configured so that the larvae moving on said inclined tracks are collected and wherein said walls are provided with traps for capturing saprophage dipters which contributes to kill the population of pest diptera and to increase larval population; and wherein said controlled openings have a diameter comprised between 1 and 50 millimeters.

9. System according to claim 7, wherein said ramps (15) are provided with a variable inclination dependent on the type of larvae used, such that said ramps can be climbed by the larvae at the pre-pupa stadium and their top is at the funnel mouth (2) of the larvae collector (12); and wherein said larvae fall directly from said ramps on said conveyor belt (10); and wherein said larvae collector (12) can be covered temporarily by lids to avoid possible penetrations of the waste inside the larvae collection and treatment circuit.

10. System according to claim 7, wherein said system for collecting and storing larvae (12) comprise an inclined pipe through which the larvae are deposited on said system of conveyor belts (10, 11) which conveys them in the storage area; wherein said larvae arrive on a first conveyor belt (10) which then conveys them on a second conveyor belt (11) from which they are conveyed to a post-treatment system.

11. Method for the batch bio-treatment of organic waste using the apparatus as described by claim 1, said method comprises the following steps:

placing a waste layer inside a container (1), placing insect larvae or eggs of one or more diptera species on said waste;

adding at pre-fixed time of about one day intervals a waste layer to be treated on the yet treated waste layer, wherein the quantity of the layer of waste added is function of the larvae development stadium, their consequent need of daily nutrition and digestive capacity;

inducing a spontaneous migration of the larvae towards suitable collecting areas using temperature and humidity control, and collecting the same larvae;

removing the treated waste batch from said container (1), continuing said preceding steps cycle until the development of the larvae is reached as they migrate outside the waste container before becoming pupas.

12. Method for the bio-treatment of organic waste according to claim 11, wherein before placing waste inside the container (1), said waste is subjected to a pre-treatment step of grinding and/or homogenization process followed by solid-liquid separation.

13. Method for the bio-treatment of organic waste according to claim 11, wherein before placing waste in the containers, said waste is additivated with *Bacillus* bacteria with or without incubation, not to promote composting, but to create an optimal mixture to promote the growth of said larvae, wherein said incubation is carried out without applicability limitations so that the waste-bacteria mix remains inside the container (1) in controlled climatic conditions useful for the development of the bacteria strains used.

14. Method for the bio-treatment of organic waste according to claim 11, wherein various kinds of organic waste are combined in order to optimize the weight and kind of constituents of collected larvae or pre-pupas.

15. Method according to claim 11, wherein said waste is organic waste derived from undifferentiated collection or undifferentiated urban solid waste and the treatment allows its primary and/or secondary bio-stabilization.

* * * * *